United States Patent [19]

Talley

[11] Patent Number: 4,939,288
[45] Date of Patent: Jul. 3, 1990

[54] METHOD OF PREPARING (R)-SUCCINIC ACID DERIVATIVES

[75] Inventor: John J. Talley, Chesterfield, Mo.

[73] Assignee: Monsanto Company, St. Louis, Mo.

[21] Appl. No.: 299,696

[22] Filed: Jan. 23, 1989

[51] Int. Cl.$^5$ ............................................. C07C 67/303
[52] U.S. Cl. ...................................... 560/81; 560/115; 560/127; 560/190; 560/193; 562/401; 502/155; 502/213; 556/18
[58] Field of Search .................. 562/401, 205; 560/61, 560/81, 85, 89, 115, 127, 190, 193; 502/155, 213

[56] References Cited

U.S. PATENT DOCUMENTS 4,142,992  3/1979  Knowles et al. .................... 252/431

OTHER PUBLICATIONS

J. O. Morrison, Asymmetric Synthesis, (1985), pp. 71–101.
W. S. Knowles, Asymmetric Hydrogenation, Acc. Chem. Res., pp. 106–112 (1983).
Christopfel et al., (1979), J. Am. Chem. Soc., 101:15, pp. 4406–4408.
Knowles et al., (1975), J. Am. Chem. Soc. 97:9, pp. 2567–2568.
Scott et al., (1981) J. Org. Chem. 46, 5086–93.
ApSimon et al., (1986), Rec. Adv. Asym. Syn. II, Tetrahedron, 43, 5173–5254.
K. Achiwa, (1978), Tetrahedron Lett., 1475–76.
Ojima et al., (1978), Chem. Lett., 567–68.
Ojima et al., (1978), Chem. Lett., 1145–1148.
Kawano et al., (1987), Tetrahedron Lett., 28, 1905–08.
J. M. Brown, (1987), Angew. Chem. Int. Ed. Engl. 26, 190–203.

*Primary Examiner*—Werren B. Lone
*Assistant Examiner*—Vera C. Clarke
*Attorney, Agent, or Firm*—James W. Williams, Jr.

[57] ABSTRACT

Method for preparing a biologically active 2-substituted succinic acid derivative involving asymmetrically catalytically hydrogenating the corresponding 2(E)-alkylidene succinate derivative in the presence of a rhodium complexed (R,R)-bisphosphine compound.

20 Claims, No Drawings

METHOD OF PREPARING (R)-SUCCINIC ACID DERIVATIVES

BACKGROUND OF THE INVENTION

1. Field of the Invention

The present invention relates to a method for preparing chiral succinates. More particularly, the present invention relates to asymmetric reduction of a 2(E)-alkylidene mono-substituted succinate to produce the corresponding (R)-succinate derivative in good yield and with excellent optical purity. The subject method involves hydrogenation of the 2(E)-alkylidene mono-substituted succinate in the presence of a rhodium complexed (R,R)-enantiomer of a bisphosphine compound represented by the formula:

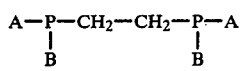

wherein A and B each independently represent substituted and unsubstituted alkyl radicals having from 1 to about 12 carbon atoms, substituted and unsubstituted cycloalkyl radicals having from about 4 to about 7 carbon atoms and substituted and unsubstituted aryl radicals; provided that such radicals provide no significant interference with the steric requirements around the phosphorus atom, and A and B are different.

2. Relevant Art

Rhodium complexed optically active bisphosphine compounds of the formula:

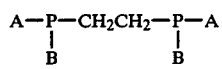

are disclosed in U.S. Pat. No. 4,142,992 to W. S. Knowles et al. Utilization of a catalyst of this type, as well as other types of catalysts, for asymmetric reduction of unsubstituted itaconic acid (methylene succinic acid) with 77% ee of the R-enantiomer being produced is disclosed in Asymmetric Synthesis, Chapter 5, J. O. Morrison, Ed., Academic Press, Inc. (1985). See also, W. S. Knowles, Asymmetric Hydrogenation, Acc. Chem. Res., 16, pp. 106–112 (1983), Christopfel et al., J. Am. Chem. Soc., 101: 15, pp. 4406–08 (1979) and Knowles et al, J. Am. Chem. Soc., 97: 9, pp. 2567–68 (1975).

It is known that asymmetric reduction of alpha-acetamidoacrylic acids

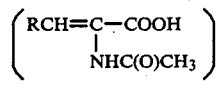

can be achieved with rhodium complexed optically active bisphosphine compounds. It is also known that although reduction of the unsubstituted olefin, i.e., where R=H, proceeds with 95% ee of the S-enantiomer being produced, the optical purity is not significantly effected, and in some cases is reduced, when R is an aliphatic hydrocarbon such as $CH_3OCH_2$—, $CH_3CH_2CH_2$—, $(CH_3)_2CH$—, and the like. See, for example, Scott et al., J. Org. Chem., 46, 5089 (1981). Reduced optical purity is also observed for substituted acetamidoacrylates wherein R is aromatic. See, for example, ApSimon et al., Rec. Adv. Asym. Syn. II, Tetrahedron, 43, p. 5181 (1986).

K. Achiwa, Tetrahedron Lett., 1475 (1978), discloses catalytic reduction of itaconic acid at pressures of 750 psig hydrogen with a catalyst generated in situ from N-acyl-3,3′-bis(diphenylphosphino) pyrrolidine and chloro rhodium octadiene dimer to produce the corresponding S-enantiomer succinic acid with optical purities ranging from 30–83%. Reduction of the sodium salt of itaconic acid with the same catalyst produced the S-enantiomer succinic acid with 92% ee. Ojima et al., Chem. Lett., 567 (1978) and Ojima et al., Chem. Lett. 1145 (1978).

Kawano et al., Tetrahedron Lett., 28, 1905 (1987) disclose reduction of itaconic acid with a ruthenium complex of optically active 2,2′-bis(diphenylphosphino)-1,1,′-binaphthyl to produce the S-enantiomer succinic acid derivative with 88% optical purity. Kawano et al., also disclose reduction of the 1-mono ester and diester with 79 and 68% ee of the S-enantiomer respectively; and reduction of 2-phenylitaconic acid and 3-methoxyphenylitaconic acid to the corresponding S-enantiomer succinic acid derivatives with 90 and 84% ee respectively.

BRIEF DESCRIPTION OF THE INVENTION

The present invention is directed to a method of preparing (R)-succinic acid derivatives represented by the formula:

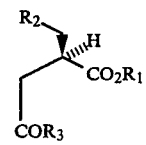

wherein $R_1$ and $R_2$ independently represent substituted and unsubstituted alkyl radicals having from 1 to about 20 carbon atoms, substituted and unsubstituted cycloalkyl radicals having from about 4 to about 10 carbon atoms and substituted and unsubstituted aryl radicals; provided that $R_2$ is not a strong electron withdrawing radical, i.e., electron withdrawing capability (sigma value) is less than about 0.27, i.e., less than that of a $COOCH_3$; [for example, see March, Advanced Organic Chemistry, 2 ed., p. 253 (1977)], and $R_3$ represents —OH, —OR—O—, O—M+, $HN^{\oplus}(R^1)_3$, —$NHR^1$, —$N(R^1)_2$ and the like, wherein $R^1$ represents radicals as defined above for $R_1$, and M represents a Group IIA metal.

The subject method involves asymmetric reduction of 2(E)-alkylidene mono-substituted succinates represented by the formula:

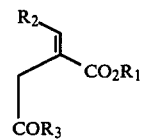

wherein $R_1$, $R_2$ and $R_3$ represent the same radicals as defined above, utilizing as catalyst a rhodium complex of an optically active bisphosphine compound represented by the formula:

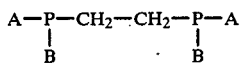

wherein A and B each independently represent substituted and unsubstituted alkyl radicals having from 1 to about 12 carbon atoms, substituted and unsubstituted cycloalkyl radicals having from about 4 to about 7 carbon atoms and substituted and unsubstituted aryl radicals; provided that such radicals provide no significant interference with the steric requirements around the phosphorus atom, and A and B are different.

The (R)-succinates, which are produced according to the subject method with high optical purities and in high yields, are useful for preparing various potent enzyme inhibitors. For example, the activity of carboxypeptidase A has been found to be strongly inhibited by 2(R)-benzyl succinic acid (Byres et al., J. Biol. Chem., 247, 606 (1977).

DETAILED DESCRIPTION OF THE INVENTION

The present invention is directed to asymmetric homogeneous hydrogenation of certain 2(E)-alkylidene mono-substituted succinic acid derivatives to produce the corresponding (R)-succinic acid derivatives which are useful for synthesizing certain enzyme inhibitors.

The 2(E)-alkylidene succinic acid derivatives can be obtained by any one of a variety of methods including by a Stobbe condensation of an aldehyde or a ketone with a dialkyl succinate ester; by a Wittig reaction of a phosphorane (also called a phosphorus ylide) succinate with an aldehyde; by a Heck reaction of a dialkyl itaconate with a halogen compound, such as iodobenzene or iodonaphthalene, in the presence of palladium diacetate; and other methods as exemplified herein.

The Stobbe condensation reaction involves condensation between a dialkyl succinate with an aldehyde or a ketone in the presence of a base. One of the ester groups, and sometimes both, is hydrolyzed in the course of the reaction. Suitable bases include NaOEt, NaH and KOCMe$_3$. A detailed description of the Stobbe condensation reaction is given in Org. React., Vol. 6, p. 1–73 (1951).

Suitable aldehydes and ketones can be represented by the formula $R^{11}CR^{111}O$ wherein $R^{11}$ and $R^{111}$ independently represent hydrogen, substituted and unsubstituted alkyl radicals having from 1 to about 20 carbon atoms, substituted and unsubstituted cycloalkyl radicals having from about 4 to about 10 carbon atoms, and substituted and unsubstituted aryl radicals, provided that such radicals, as a whole, are not strong electron withdrawing radicals. Strong electron withdrawing radicals are those wherein the electron withdrawing ability of the radical is greater than or equal to that of a COOCH$_3$ radical and further provided that $R^{11}$ and $R^{111}$ are not both hydrogen.

In the Wittig reaction, the desired olefin is formed from an aldehyde or ketone treated with a phosphorane prepared by treating a phosphonium salt with a base, the phosphonium salt being prepared from a phosphine and an alkyl halide in which the halogen-bearing carbon contains at least one hydrogen. Suitable aldehydes and ketones can be represented by the above defined formula $R^{11} CR^{111} O$ wherein $R^{11}$ and $R^{111}$ are as defined above. Suitable phosphoranes include substituted and unsubstituted, saturated and unsaturated aliphatic, alicyclic and aromatic derivatives. Electron withdrawing groups in the alpha-position stabilize the phosphorane. The reaction is carried out in solution utilizing an inert solvent such as ether, tetrahydrofuran or dioxane for a time period of from about 0.1 to about 120 hours. Concentrations of reactants are not critical and can range from about 1 to about 3 moles of the phosphorane to about one mole of aldehyde or ketone. The Wittig reaction is described in detail in Org. React., 14, 270–490 (1965).

The Heck reaction involves catalyzed coupling of an unsaturated organic halide and a dialkyl succinate. The Heck reaction is also disclosed in U.S. Pat. Nos. 3,413,352, 3,574,777, 3,527,794, 3,700,727, 3,705,919, 3,763,213, 3,783,140, 3,922,299 and 3,988,358 which are hereby incorporated by reference. The catalyst suitable for the Heck reaction is a Group VIII metal, a preferred group being palladium, nickel and rhodium. A most preferred metal catalyst is palladium. Examples of suitable palladium catalysts include palladium diacetate, tetrakis(triphenylphosphine) palladium(O) and palladium dibenzylideneacetone. The preferred palladium catalyst is palladium diacetate. The catalyst concentration is not critical and can vary widely depending on reaction conditions. The concentration of the catalyst is in the range of 0.01 to 5.0 mole % based on the unsaturated organic halide. The preferred range is 1.0 to 2.0 mole % based on the unsaturated organic halide.

Optionally, a trivalent phosphorus or arsenic ligand can be used with the Group VIII metal catalyst. A trivalent phosphorus or arsenic ligand suitable for the present invention is the trialkyl, triaryl, trialkoxy, halo or triphenoxy derivative of phosphorus or arsenic or mixtures thereof. Examples of these ligands are triphenylphosphine, tri-n-butylphosphine, diphenylmethylphosphine, diphenylmethoxyphosphine, tri-methylphosphite, triethylphosphine, tri-ortho-tolylphosphine, phenyldi-n-butoxyphosphine, phosphorus trichloride, phenyldichlorophosphine, arsenic tribromide, triphenylarsine and triphenyl arsenite. The ratio of the ligand to the metal catalyst is not critical. The ratio can vary in the range of about 0.5:1 to about 10:1 mole ratio of ligand to metal catalyst.

The Heck reaction takes place in solution, in a slurry or neat. A preferred Heck reaction can be carried out using the unsaturated organic halide, a palladium catalyst, a phosphorus or arsenic ligand and a polar organic solvent that is inert to the reactants. Suitable polar organic solvents include N-methylpyrrolidone, acetonitrile, propionitrile, N-methyl formamide and dimethyl formamide (DMF). A preferred solvent is DMF.

The reaction temperature is any temperature sufficient to sustain the reaction and is in the range of about 50° C. to 175° C. A preferred reaction temperature range is from about 60° C. to about 110° C.

The Heck reaction can optionally take place in the presence of a base to absorb the acid generated in the reaction. Suitable bases are weak organic or inorganic bases that are inert to the reactants. Examples of such organic bases include trialkyl amines such as triethylamine and tributylamine and other inorganic bases such as sodium acetate, sodium bicarbonate and potassium bicarbonate. A preferred base is triethyl amine.

A detailed description of the Heck reaction is given in Heck, Palladium Reagents in Organic Syntheses, Academic Press (1985).

Asymmetric homogeneous hydrogenation of the above-described 2(E)-alkylidene succinic acid derivatives to produce the R-enantiomer of the corresponding succinate in high yield with good optical purity is accomplished utilizing a rhodium complex of an optically active (R,R)-bisphosphine compound having the formula:

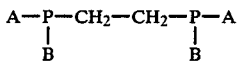

wherein A and B are the same as defined above. These catalysts and their method of preparation are described in detail in U.S. Pat. No. 4,142,992. Preparation of numerous bisphosphine compounds are also described in U.S. Pat. No. 4,008,281. Both of these patents are incorporated herein by reference.

Particularly preferred R,R-bisphosphine compounds for utilization in the present invention are characterized by the structural formula:

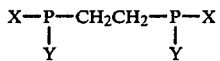

wherein X represents substituted and unsubstituted phenyl, Y represents substituted and unsubstituted 2-alkoxyphenyl wherein the alkoxy has from 1 to 6 carbon atoms; provided that such substituents provide no significant interference with the steric requirements around the phosphorus atom and X and Y are different.

Still more particularly preferred bis-phosphine compounds for utilization in the present invention are characterized by the structurl formula:

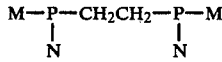

wherein
M represents

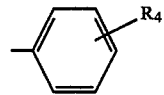

N represents

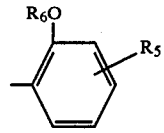

$R_4$ and $R_5$ each independently represent hydrogen, halogen, alkyl radicals having from 1 to 6 carbon atoms, and alkoxy radicals having from 1 to 6 carbon atoms, and $R_6$ represents normal alkyl radicals having from 1 to 6 carbon atoms; provided that M and N are different. A particularly preferred novel compound provided by the present invention is 1,2-bis(p-anisylphenylphosphino)ethane which can readily be prepared from its precursor compound, 1,2-bis(o-anisylphenylphosphinyl)ethane.

Other exemplary bisphosphine compounds which may be utilized in the method of this invention are:
1,2-bis(o-anisyl-4-methylphenylphosphino)ethane 1,2-bis(o-anisyl-4-chlorophenylphosphino)ethane
1,2-bis(o-anisyl-3-chlorophenylphosphino)ethane
1,2-bis(o-anisyl-4bromophenylphosphino)ethane
1,2-bis(2-methoxy-5-chlorophenyl)-phenylphosphino)ethane
1,2-bis[(2-methoxy-5-bromophenyl)-phenylphosphino]ethane
1,2-bis(2-ethoxyphenylphenylphosphino)ethane
1,2-bis[o-anisyl-(p-phenylphenyl)phosphino]ethane
1,2[(2-methoxy-4-methylphenyl)-phenylphosphino]ethane
1,2-bis(2-ethoxyphenyl-4-chlorophenylphosphino)ethane
1,2-bis(o-anisyl-2-methylphenylphosphino)ethane
1,2-bis(o-anisyl-4-ethylphenylphosphino)ethane
1,2-bis(o-anisyl-3-ethylphenylphosphino)ethane
1,2-bis(o-anisyl-3-phenylphenylphosphino)ethane For these bisphosphine compounds to be useful in the asymmetric hydrogenation reaction of the present invention, they must be utilized as the optically active (R,R)-enantiomorph.

Soluble rhodium compounds that can be utilized include rhodium tri-chloride hydrate, rhodium tribromide hydrate, rhodium sulfate, organic rhodium complexes with ethylene, propylene, etc., and bis olefins such as 1,5-cyclooctadiene and 1,5-hexadiene, bicyclo[2.2.1-]hepta-2,5-diene and other dienes which can form bidentate ligands, or an active form of metallic rhodium that is readily solubilized.

Preferably, the bisphosphine ligand is present in a ratio of about 0.5 to about 2.0 preferably 1.0, moles of bis phosphine ligand per mole of rhodium metal. In practice, it is preferred to have the optically active catalyst in a solid form for purposes of handling and storage. It has been found that these results can be obtained with solid, cationic coordination metal complexes.

Cationic coordination metal complexes containing one mole of the optically active bis-phosphine ligand per mole of metal and a chelating bis olefin represent preferred embodiments of the catalysts of the present invention. For instance, using organic rhodium complexes, as described above, one can prepare such cationic coordination rhodium complexes by slurrying the organic rhodium complex in an alcohol, such as ethanol, adding one mole per mole of rhodium of the optically active bisphosphine compound so that an ionic solution is formed, followed by the addition of a suitable anion, such as, for instance, tetrafluoroborate, tetraphenylborate or any other anion that will result in the precipitation or crystallization of a solid, cationic coordination metal complex either directly from the solvent or upon treatment in an appropriate solvent.

For instance, exemplary cationic coordination metal complexes are cyclooctadiene-1,5-[1,2-bis(o-anisylphenylphosphino)ethane]rhodium tetrafluoroborate, cyclooctadiene-1,5[1,2-bis(o-anisylphenylphosphino)ethane]rhodium tetraphenyl-borate and bicyclo[2.2.1]hepta-2,5-diene [1,2-bis(o-anisylphenylphosphino)ethane]rhodium tetrafloroborate.

In the following examples, melting points were determined on a Fischer-Johns melting point apparatus and are uncorrected. Infrared spectra were measured on an IBM IR30 instrument, absorbance positions are reported in $cm^{-1}$. Proton and carbon magnetic resonance spectra were recorded on a Varian VXR-300)) spectrometer using tetramethylsilane as internal standard.

Liquid chromatography was performed on a Spectra Physics chromatography system.

The optical purity of 2(R)-benzylsuccinic acid derivatives was determined by conversion to 2(R)-benzylsuccinic acid by hydrolysis with aqueous lithium hydroxide in methanol. After isolation of the acid, the optical rotation was obtained and compared to the value of optically pure 2(R)-benzylsuccinic acid, $[alpha]^{25}D = +27°$ (c=2.0, ethyl acetate). See Cohen, S. G.; Milovanovic, A. J. Am. Chem. Soc. 1968, 90, 3495.

Optical purity can also be determined by the addition of the chiral NMR shift reagent tris[3-(heptafluorobutyryl)d-camphorato]europium III to a solution of the succinic acid methyl ester in deuteriochloroform and then integration of the methyl ester resonance, or by HPLC analysis on a Chiracel OC column eluting with hexane:isopropyl alcohol solvent (98:2 volume to volume ratio) at 1 mL/minute monitoring at 210 nm.

EXAMPLE I

Preparation of 2(E)-Isobutylidene Mono-Methyl Succinate by Stobbe Condensation A 1000 mL round-bottomed flask equipped with a reflux condenser, nitrogen inlet, constant pressure addition funnel and mechanical stirrer was charged with tert-butyl alcohol (300 mL) and then potassium tert-butoxide (Aldrich) (49.4 g, 0.44 mol) was added portion wise over ca. 0.5 hour (this prevents clumping of the tert-butoxide). To this stirring solution was added dropwise over ca. 45 minutes a solution of isobutyraldehyde (28.1 g, 0.4 mol) and dimethyl succinate (73.1 g, 0.5 mol) in 50 mL of tert-butyl alcohol. The solution was then warmed to 50° C. for a period of 2 h and then concentrated on a rotary evaporator. The thick oil was diluted with 3N HCl, then extracted with ether (3×100 mL), and the combined ethereal layer was then extracted with saturated aqueous sodium bicarbonate (3×100 mL). The combined aqueous extract was then acidified to pH=1 with HCl and re-extracted with ether (3×100 mL). The combined ethereal phase was washed with brine and dried over anhydrous magnesium sulfate, filtered, and stripped on a rotary evaporator. The last traces of ether were removed on a vacuum pump overnight. In the morning the crude product had solidified into a white mass, 66.2 g 89% yield. The nmr of this material showed that some of the undesired (Z)-isomer was present, ca. 15% The crude solid was crushed and then washed with n-hexane. This removed the oily substance that was trapped on the solid, providing a nice free flowing powder. The solid was taken up in 290 mL of boiling hexane and allowed to stand. The product initially oiled out but with some swirling and scratching crystallized. The material was then isolated by filtration on a Buchner funnel, was washed with some cold hexane, and then dried in a vacuum drying oven for a couple of hours. The material thus obtained was a very nice free flowing powder that gave a nmr consistent with the desired product, mp 72°-74° C., total yield 46 g, 62%.

Asymmetric Reduction of 2(E)-Isobutylidene mono-Methyl Succinate, Preparation of 2(R)-Isobutyl Mono-Methyl Succinate A Fisher-Porter bottle was charged with the above mono-methyl ester (10.00 g, 0.0538 mol), 50 mL of degassed methanol, and 300 mg of rhodium (R,R)DiPAMP (R,R)-(1,2-ethanediyl bis[(O-methoxyphenyl)phenylphosphine]) catalyst. After 5 nitrogen purges (40 psig) the solution was purged 5× with hydrogen (40 psig) and then allowed to hydrogenate at room temperature for 24 h. The hydrogen was displaced with nitrogen and the bottle opened and the methanol removed on a rotary evaporator. The catalyst was removed by passing through a silica gel column eluting with hexane/ethyl acetate 1:1. Removal of the solvent gave the crude product as an oil. The oil was pumped on a vacuum pump for ca. 1 h and nmr was obtained that looked perfect for the reduced compound. A sample dissolved in ethyl acetate had a specific rotation $[\alpha]_D^{20} = +14.9°$, 9.60 g, 95%.

EXAMPLE 2

Preparation of 2(E)-Benzylidene Dimethyl Succinate by Heck Reaction, Palladium Catalyzed Coupling of Dimethyl Itaconate with Iodobenzene A 250 mL 3-necked round-bottomed flask equipped with reflux condenser, N₂ inlet and mechanical stirrer was charged with iodobenzene (40.8 g, 0.2 mol), dimethyl itaconate (31.6 g, 0.2 mol), triethylamine (25.2 g, 0.25 mol) palladium (II) acetate (0.448 g, 2.0 mmol), and triphenylphosphine(1.04 g, 4.0 mmol). The mixture was heated to 100° C. for 6 h whereupon the reaction mixture formed a dark paste. The mixture was cooled to ambient temperature, diluted with ethyl acetate and then poured into a separatory funnel. The solution was washed with 3N HCl, water, saturated aqueous NaHCO₃, brine and dried over anhydrous M₉SO₄. The solution was filtered, concentrated on a rotary evaporator and the residue vacuum distilled through a 12″ Vigeraux column; recovered 6.34 g of dimethyl itaconate, bp 55°-70° D., 0.1 mm and then the desired product boiled at 138° C. 0.1 mm to give 34.25 g, 84% based on recovered dimethyl itaconate.

EXAMPLE 3

Preparation of 2(E)-Ethylidene Mono-Methyl Succinate by Wittig Reaction

Preparation of 2-Triphenylphosphoranylidene Succinic Anhydride

A 500 mL 3-necked round-bottom flask equipped with a mechanic stirrer, N₂ inlet and solids addition funnel was charged with triphenylphosphine (52.5 g, 0.2 mol) in 200 mL of reagent grade acetone. From the addition funnel was added maleic anhydride (19.5 g, 0.2 mol) over a 0.5 h period. After ca. 0.5 h at room temperature, the product began to separate. The mixture was stirred at room temperature for 3 h and then the product isolated by filtration on a Buchner funnel. The solid was washed with acetone and air dried to give 54 g, 75% of product, mp 165° C. (dec). (CDCl₃) 2.17 (3H, ½ mole of acetone in crystal), 3.21 (2H, s), 7.60 (15H, m).

Preparation of 2-Triphenylphosphoranylidene Mono-Methyl Succinate

A 500 mL 3-necked round-bottomed flask equipped with a reflux condenser, nitrogen inlet and mechanical stirrer was charged with 2-triphenylphosphoranylidene succinic anhydride (38.1 g, 0.106 mol) and 300 mL of anhydrous methanol. The slurry was stirred at room temperature for 14 h whereupon a homogeneous solution was obtained. The solvent was removed on a rotary evaporator and the oily residue taken up on methyl ethyl ketone and then cooled to 5° C. in an ice bath whereupon crystals formed that were isolated by filtration and dried in vacuum, 41.4 g. Examination of the $^1$H NMR revealed that the desired product had crystallized with ca. 1 mole of methyl ethyl ketone. mp 144° C. $^1$H NMR (CDCl$_3$) 2.89 (2H, d, J=15 Hz), 3.35 (3H, s), 7.60 (15H, m).

Condensation of 2-triphenylphosphoranylidene mono-methyl succinate with acetaldehyde at room temperature for five days resulted in formation of 2(E)-Ethylidene mono-methyl succinate in 67% isolated yield. The (Z) isomer could not be detected by NMR spectroscopy.

EXAMPLE 4

Preparation of 4(4-Methoxybenzyl) Itaconate

A 250 ml one-necked round bottomed flask equipped with reflux condenser, nitrogen inlet, and magnetic stir bar was charged with itaconic anhydride (33.6 g, 0.3 mol) toluene (100 ml) and 4-methoxybenzyl alcohol (41.5 g, 0.3 mol). The solution was then warmed to reflux for 60 minutes and then cooled to room temperature. The solution was poured into a 500 ml Erlenmeyer flask, diluted with 100 ml of hexane and allowed to stand whereupon crystals of pure monoester formed. The product was isolated by filtration on a Buchner funnel and air dried to give 45.4 g, 61% of material with mp 83°-85° C., a second crop, 12.9 g, 17% was isolated after cooling of the filtrate in an ice bath.

EXAMPLE 5

Preparation of Methyl 4(4-Methoxybenzyl) Itaconate

A 250 ml three-necked round bottomed flask equipped with reflux condenser, nitrogen inlet, serum cap and magnetic stir bar was charged with 4(4-methoxybenzyl) itaconate (12.5 g, 0.05 mol) and 100 ml of toluene. To this stirring solution was added 1,5-diazabicyclo[4.3.0]non-5-ene (6.21 g, 0.05 mol) and then a solution of methyl iodide (7.38 g, 0.05 mol) in 25 ml of toluene via syringe. The solution was stirred at room temperature for one hour and then poured into a separatory funnel. The solution was washed with water and then dried over anhydrous magnesium sulfate, filtered, and the solvent removed in vacuo. This gave a clear colorless oil, 11.9 g, 95% whose nmr was consistent with the assigned structure.

EXAMPLE 6

Preparation of Methyl Itaconate

A 50 ml round-bottomed flask equipped with reflux condenser, nitrogen inlet and magnetic stir bar was charged with methyl 4(4-methoxybenzyl) itaconate (4.00 g, 16 mmol), toluene (10 ml), and trifluoroacetic acid (2.50 g, 22 mmol). The solution was kept at room temperature for 18 hours and then volatiles were removed in vacuo. The residue was taken up in ethyl acetate and extracted three times with saturated aqueous sodium bicarbonate solution. The combined aqueous extract was acidified to pH=1 with aqueous potassium bisulfate and then extracted three times with ethyl acetate. The combined ethyl acetate solution was washed with saturated aqueous sodium chloride, dried over anhydrous magnesium sulfate, filtered, and concentrated in vacuo. The residue was then vacuum distilled to give 2.13 g, 74% of pure product, bp 85-87 @ 0.1 mm.

EXAMPLE 7

The 2(E)-alkylidene succinic acid derivatives set forth in Table 1 were prepared as indicated therein according to one of the procedures set forth in Examples 1-6.

TABLE 1

2-Alkylidene Succinic Acid Derivatives

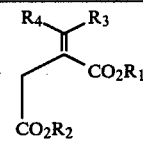

| Entry | R$_1$ | R$_2$ | R$_3$ | R$_4$ | mp(°C.) (bp °C.) | Method of Preparation |
|---|---|---|---|---|---|---|
| 1. | CH$_3$ | (CH$_3$)$_3$C | H | C$_6$H$_5$CH$_2$ | Oil | b |
| 2. | CH$_3$ | H | H | C$_6$H$_5$CH$_2$CH$_2$ | 163-165 | a |
| 3. | C$_6$H$_5$CH$_2$ | H | H | C$_6$H$_5$ | 92-93 | b |
| 4. | CH$_3$ | H | H | CH$_3$ | <40(85/0.1 mm) | b |
| 5. | CH$_3$ | CH$_3$ | H | C$_6$H$_5$ | (138/0.1 mm) | c |
| 6. | CH$_3$ | H | H | C$_6$H$_5$ | 122-124 d | a |
| 7. | H | H | H | C$_6$H$_5$ | 187-189 | e |
| 8. | CH$_3$ | H | CH$_3$ | CH$_3$ | 55-57 | a |
| 9. | CH$_3$ | H | H | C$_6$H$_{11}$ | 75-77 | a |
| 10. | CH$_3$ | H | H | —CH(CH$_3$)$_2$ | 72-74 | a |
| 11. | CH$_3$ | H | H | —C$_6$H$_4$OCH$_2$C$_6$H$_5$ | 121-122 | b |
| 12. | H | CH$_3$OC$_6$H$_4$CH$_2$ | H | H | 83-85 | f |
| 13. | CH$_3$ | CH$_3$OC$_6$H$_4$CH$_2$ | H | H | Oil | g |
| 14. | CH$_3$ | H | H | H | (85-87/0.1 mm) | h | a = Stobbe condensation.
b = Wittig reaction.
c = Heck reaction.
d = Dicyclohexylammonium salt.
e = Derivative of Entry 6
f = Method of Example 4
g = Method of Example 5
h = Method of Example 6

EXAMPLE 8

The 2(R)-succinic acid derivatives set forth in Table 2 were prepared by asymmetrically hydrogenating the corresponding 2(E)-alkylidene succinate utilizing the procedure set forth in Example 1.

TABLE 2
2(R)-Alkyl Succinic Acid Derivatives

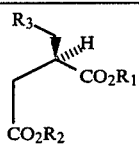

| Entry | $R_1$ | $R_2$ | $R_3$ | mp(°C.) (bp °C.) | $[\alpha]_D^{20}$ | ee |
|---|---|---|---|---|---|---|
| 1. | $CH_3$ | H | H | 95–97 a (85–90/.1 mm) | b | 88 |
| 2. | $CH_3$ | H | $CH_3$ | oil | b | b |
| 3. | $CH_3$ | H | $C_6H_5$ | 116–118 a | +26 c | >97 |
| 4. | $CH_3$ | $CH_3$ | $C_6H_5$ | oil | b | 70 |
| 5. | H | H | $C_6H_5$ | 166–168 | +26.3 | >97 |
| 6. | $CH_3$ | H | $CH(CH_3)_2$ | 108.0–109.5 a | +14.9 | 76 |
| 7. | $CH_3$ | H | $C_6H_{11}$ | oil | +20.1 | b | a = Dicyclohexylammonium salt.
b = Not determined.
c = Optical rotation of the diacid.

EXAMPLE 9

The following substrates were reduced according to the procedure set forth in Example 1. Results are reported in Table 3. Entries 1–4 are comparative and illustrate no increase in optical purity when an olefin is substituted. Entries 5–8 illustrate significant unexpected increases in optical purity when the olefin is substituted.

TABLE 3

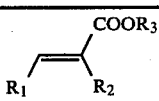

| Entry No. | $R_1$ | $R_2$ | $R_3$ | % ee |
|---|---|---|---|---|
| 1 | H | —NHCOCH$_3$ | H | 93 (S) |
| 2 | H | —NHCOCH$_3$ | $CH_3$ | 93 (S) |
| 3 | $C_6H_5$ | —NHCOCH$_3$ | H | 94 (S) |
| 4 | $C_6H_5$ | —NHCOCH$_3$ | $CH_3$ | 96 (S) |
| 5 | H | —CH$_2$COOH | H | 35 (R) |
| 6 | H | —CH$_2$COOH | $CH_3$ | 88 (R) |
| 7 | $C_6H_5$ | —CH$_2$COOH | H | 74 (R) |
| 8 | $C_6H_5$ | —CH$_2$COOH | $CH_3$ | >97 (R) |

While the invention has been described herein with regard to certain specific embodiments, it is to be understood that variations and modifications thereof may be made by those skilled in the art without departing from the spirit and scope of the invention.

What is claimed is:

1. A method for preparing 2(R)-substituted succinic acid derivatives comprising asymmetrically cataytically hydrogenating the corresponding 2(E)-alkylidene succinate derivative in the presence of a rhodium complexed (R,R)-bisphoshine compound of the formula:

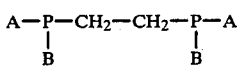

wherein A and B each independently represent substituted and unsubstituted alkyl radicals having from 1 to about 12 carbon atoms, substituted and unsubstituted cycloalkyl radicals having from about 4 to about 7 carbon atoms and substituted and unsubstituted aryl radicals; provided that such radicals provide no significant interference with the steric requirements around the phosphorus atom, and A and B are different.

2. Method of claim 1 wherein the R-succinic acid derivatives are represented by the formula:

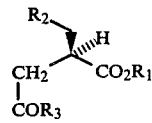

wherein $R_1$ and $R_2$ independently represent substituted and unsubstituted alkyl radicals having from 1 to about 20 carbon atoms, substituted and unsubstituted cycloalkyl radicals having from about 4 to about 10 carbon atoms and substituted and unsubstituted aryl radicals, provided that $R_2$ is not a strong electron withdrawing radical, and $R_3$ represents —OH, OR$^1$, —O$^-$, O$^{-M+}$, HN$^{\oplus}$(R$^1$)$_3$, —NHR$^1$, N(R$^1$)$_2$, wherein R$^1$ represents radicals as defined for $R_1$ and M is a Group II A metal.

3. Method of claim 1 wherein the 2(E)-alkylidene succinate derivative is represented by the formula:

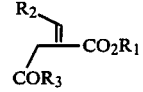

wherein $R_1$ and $R_2$ independently represent substituted and unsubstituted alkyl radicals having from 1 to about 20 carbon atoms, substituted and unsubstituted cycloalkyl radicals having from about 4 to about 10 carbon atoms and substituted and unsubstituted aryl radicals, provided that $R_2$ is not a strong electron withdrawing radical, and $R_3$ represents —OH, OR$^1$, —O$^-$, O$^{-M+}$, HN$^{\oplus}$(R$^1$)$_3$, —NHR$^1$, N(R$^1$)$_2$, wherein R$^1$ represents radicals as defined for $R_1$ and M is a Group II A metal.

4. Method of claim 1 wherein the bis phosphine is of the formula:

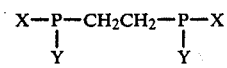

wherein X represents substituted and unsubstituted phenyl, Y represents substituted and unsubstituted 2-alkoxyphenyl wherein the alkoxy group has from 1 to about 6 carbon atoms; provided that such substituents provide no significant interference with the steric requirements around the phosphorus atom, and X and Y are different.

5. Method of claim 1 wherein the bisphosphine compound is represented by the structural formula:

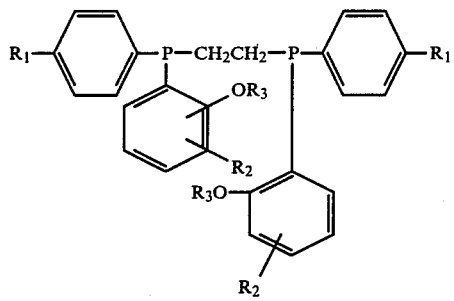

wherein $R_1$ and $R_2$ each independently represent hydrogen halogen, alkyl having from 1 to about 6 carbon atoms and alkoxy having from 1 to about 6 carbon atoms, and $R_3$ represents alkyl radicals having from 1 to about 6 carbon atoms.

6. Method of claim 1 wherein said bisphosphine compound is 1,2-bis(O-anisylphenyl phosphine) ethane.

7. Method of claim 1 wherein the rhodium coordinated catalyst of the bisphosphine compound includes a chelating bis olefin.

8. Method of claim 7 wherein the chelating bis olefin is cyclooctadiene.

9. Method of claim 1 wherein the catalyst includes a chelating bis olefin and an anion.

10. Method of claim 9 wherein the chelating bis olefin is cyclooctadiene and the anion is tetrafluoroborate.

11. In a method for preparing 2-substituted succinic acid derivatives wherein one enantiomer is produced in excess of the other by asymmetrically catalytically hydrogenating 2-substituted alkylidene succinates, the improvement which comprises producing the (R)-enantioner in excess by asymmetrically catalytically hydrogenating the (E)-configuration of the 2-substitued alkylidene succinate utilizing as the hydrogenation catalyst a rhodium complex of an (R, R)-enantiomer of a bisphosphine compound represented by the formula:

$$A-P-CH_2-CH_2-P-A$$
$$\phantom{A-P-}|\phantom{CH_2-CH_2-}|$$
$$\phantom{A-P-}B\phantom{CH_2-CH_2-}B$$

wherein A and B each independently represent substituted and unsubstituted alkyl radicals having from 1 to about 12 carbon atoms, substituted and unsubstituted cycloalkyl radicals having from about 4 to about 7 carbon atoms and substituted and unsubstituted aryl radicals; provided that such radicals provide no significant interference with the steric requirements around the phosphorus atom, and A and B are different.

12. Method of claim 11 wherein the R-succinic acid derivatives are represented by the formula:

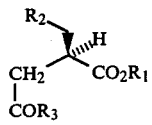

wherein $R_1$ and $R_2$ independently represent substituted and unsubstituted alkyl radicals having from 1 to about 20 carbon atoms, substituted and unsubstituted cycloalkyl radicals having from about 4 to about 10 carbon atoms and substituted and unsubstituted aryl radicals, provided that $R_2$ is not a strong electron withdrawing radical, and $R_3$ represents —OH, $OR^1$, —$O^-$, $O^{-M+}$, $HN\oplus(R^1)_3$, —$NHR^1$, $N(R^1)_2$, wherein $R^1$ represents radicals as defined for $R_1$ and M is a Group II A metal.

13. Method of claim 11 wherein the 2(E)-alkylidene succinate derivative is represented by the formula:

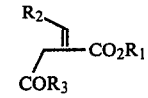

wherein $R_1$ and $R_2$ independently represent substituted and unsubstituted alkyl radicals having from 1 to about 20 carbon atoms, substituted and unsubstituted cycloalkyl radicals having from about 4 to about 10 carbon atoms and substituted and unsubstituted aryl radicals, provided that $R_2$ is not a strong electron withdrawing radical, and $R_3$ represents —OH, $OR^1$, —$O^-$, $O^{-M+}$, $HN\oplus(R^1)_3$, —$NHR^1$, $N(R^1)_2$, wherein $R^1$ represents radicals as defined for $R_1$ and M is a Group II A metal.

14. A method of claim 11 wherein the bis phosphine is of the formula:

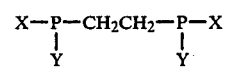

wherein X represents substituted and unsubstituted phenyl, Y represents substituted and unsubstituted 2-alkoxyphenyl wherein the alkoxy group has from 1 to about 6 carbon atoms; provided that such substituents provide no significant interference with the steric requirements around the phosphorus atom, and X and Y are different.

15. Method of claim 11 wherein the bisphosphine compound is represented by the structural formula:

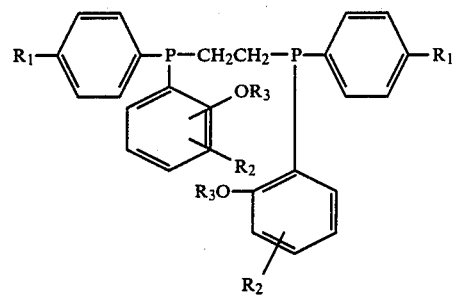

wherein $R_1$ and $R_2$ each independently represent hydrogen halogen, alkyl having from 1 to about 6 carbon atoms and alkoxy having from 1 to about 6 carbon atoms, and $R_3$ represents alkyl radicals having from 1 to about 6 carbon atoms.

16. Method of claim 11 wherein said bisphosphine compound is 1,2-bis(O-anisylphenyl phosphine) ethane.

17. Method of claim 11 wherein the rhodium coordinated catalyst of bisphosphine compound includes a chelating bis olefin.

18. Method of claim 17 wherein the chelating bis olefin is cyclooctadiene.

19. Method of claim 11 wherein the catalyst includes a chelating bis olefin and an anion.

20. Method of claim 19 wherein the chelating bis olefin is cyclooctadiene and the anion is tetrafluoroborate.

* * * * *